United States Patent
Lorente Bonde-Larsen et al.

(10) Patent No.: US 8,722,920 B2
(45) Date of Patent: May 13, 2014

(54) PROCESS FOR OBTAINING 3,3-DIPHENYLPROPYLAMINES

(75) Inventors: Antonio Lorente Bonde-Larsen, Boecillo-Valladolid (ES); Pablo Martín Pascual, Boecillo-Valladolid (ES); Mario Laderas Muñoz, Boecillo-Valladolid (ES); Luis Gerardo Gutiérrez Fuentes, Boecillo-Valladolid (ES)

(73) Assignee: Crystal Pharma S.A.U., Boecillo-Valladolid (ES)

( * ) Notice: Subject to any disclaimer, the term of this patent is extended or adjusted under 35 U.S.C. 154(b) by 173 days.

(21) Appl. No.: 13/387,573

(22) PCT Filed: Jul. 26, 2010

(86) PCT No.: PCT/EP2010/060817
§ 371 (c)(1),
(2), (4) Date: May 7, 2012

(87) PCT Pub. No.: WO2011/012584
PCT Pub. Date: Feb. 3, 2011

(65) Prior Publication Data
US 2012/0220797 A1  Aug. 30, 2012

(30) Foreign Application Priority Data

Jul. 27, 2009 (EP) .................................... 09382123

(51) Int. Cl.
*C07C 229/38* (2006.01)
*C07C 63/04* (2006.01)

(52) U.S. Cl.
USPC ............................................ 560/36; 562/441

(58) Field of Classification Search
USPC ............................................ 560/36; 562/441
See application file for complete search history.

(56) References Cited

U.S. PATENT DOCUMENTS 6,809,214 B2 * 10/2004 Meese ............................. 560/36

FOREIGN PATENT DOCUMENTS

| EP | 1 289 929 | 3/2012 |
|---|---|---|
| WO | WO 99/58478 B1 | 11/1999 |
| WO | WO 01/96297 A2 | 12/2001 |
| WO | WO 2007/017544 A2 | 2/2007 |
| WO | WO 2007/138440 A1 | 12/2007 |
| WO | WO 2007/140986 A1 | 12/2007 |

OTHER PUBLICATIONS

Braun, L.M. et al., "Dimethyl Sulfide-Borane. A Convenient Hydroborating Agent", Journal of Organic Chemistry, 1971, vol. 36, No. 16, pp. 2388-2389.

Gómez-Gallego, M. et al., "On the Reduction of α,β-Unsaturated (Group 6) Carbene Complexes by $NaBH_4^1$", Tetrahedron, 2000, vol. 56, pp. 4893-4905.

Manninen, K. and Karjalainen, A., "Hydride Transfer Reaction Products in the Aminomethylation of Styrene", Acta Chemica Scandinavica, 1986, B40, pp. 190-195.

Masuyama, Y. et al., "Palladium-Catalyzed Allylic Amination of Allylic Alcohols with Tin(II) Chloride and Triethylamine", Chemistry Letters, 1995, No. 12, pp. 1121-1122.

Nilvebrant, L. et al., "Antimuscarinic Potency and Bladder Selectivity of PNU-200577, a Major Metabolite of Tolterodine", Pharmacology and Toxicology, 1997, vol. 81, pp. 169-172.

Schmidt, U. and Wild, J., "Totalsynthese von Hexaacetylcelenamid A", Liebigs Ann. Chem., 1985, pp. 1882-1894.

Suárez, S. et al., "Lanthanide luminescent mesomorphic complexes with macrocycles derived from diaza-18-crown-16†‡", New Journal of Chemistry, 2005, vol. 29, issue 16, pp. 1323-1334.

(Continued)

*Primary Examiner* — Kamal Saeed
*Assistant Examiner* — Janet L Coppins
(74) *Attorney, Agent, or Firm* — Gary J. Gershik; Cooper & Dunham LLP

(57) ABSTRACT

The invention relates to a process for obtaining 3,3-diphenylpropylamines of general formula (I), particularly Fesoterodine, as well as their enantiomers, solvates and salts, comprising a chemoselective reduction of the acid group against the ester group in compounds of general formula (V), wherein $R_1$ is $C_1$-$C_8$ alkyl; and $R_3$ and $R_4$, independently of one another, represent H or $C_1$-$C_8$ alkyl, or together form a ring of 3 to 7 members with the nitrogen to which they are bound. The invention also relates to the compounds of formula (V), as well as their enantiomers, solvates and salts.

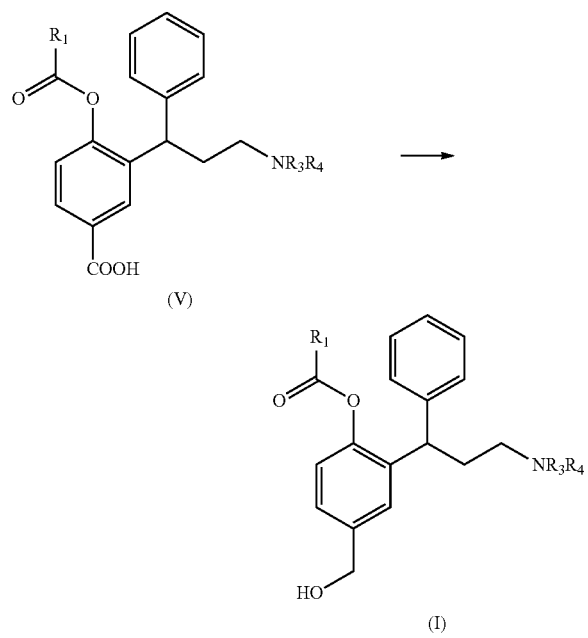

20 Claims, No Drawings

(56) References Cited

OTHER PUBLICATIONS

Yoon, N.M. and Pak, C.S., "Selective Reductions. XIX. The Rapid Reaction of Carboxylic Acids with Borane-Tetrahydrofuran. A Remarkably Convenient Procedure for the Selective Conversion of Carboxylic Acids to the Corresponding Alcohols in the Presence of Other Functional Groups", Journal of Organic Chemistry, 1973, vol. 38, No. 16, pp. 2786-2792.

International Search Report issued by the International Searching Authority (ISA/O.E.P.M.) on Sep. 9, 2010 in connection with International Application No. PCT/EP2010/060817.

European Search Report issued by the European Patent Office on Dec. 15, 2009 in connection with European Patent Application EP 09 38 2123.

* cited by examiner

PROCESS FOR OBTAINING 3, 3-DIPHENYLPROPYLAMINES

RELATED APPLICATIONS

This application is a §371 national stage of PCT International Application No. PCT/EP2010/060817, filed Jul. 26, 2010, claiming priority of European Patent Application No. EP 09382123.9, filed Jul. 27, 2009, the contents of each of which are hereby incorporated by reference into this application.

FIELD OF THE INVENTION

The invention relates to a process for obtaining 3,3-diphenylpropylamines, particularly Fesoterodine, as well as their enantiomers, solvates and salts.

BACKGROUND OF THE INVENTION 3,3-diphenylpropylamines which act as muscarinic receptor antagonists and are useful in the treatment of urinary incontinence and other symptoms of urinary bladder hyperactivity are known. Said compounds include N,N-diisopropyl-3-(2-hydroxy-5-methylphenyl)-3-phenylpropylamine, the (R) enantiomer of which is known as Tolterodine.

Another compound with a similar structure is 5-hydroxymethyl tolterodine, which is the main metabolite of Tolterodine (Nilvebrant et al. *Pharmacol. Toxicol.* 1997, 81(4), 169-172), a potent muscarinic receptor antagonist (WO 94/11337).

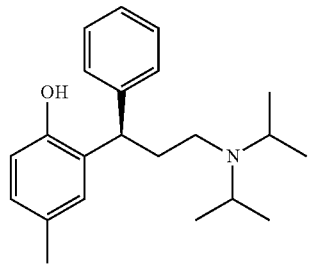

Tolterodine

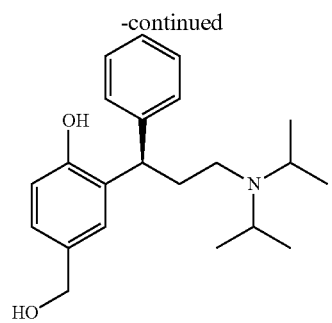

5-hydroxymethyl Tolterodine

WO 99/058478 describes the therapeutic usefulness of phenolic esters of said main metabolite of Tolterodine, especially of isobutyric acid 2-((R)-3-N,N-diisopropylamino-1-phenylpropyl)-4-(hydroxymethyl)phenyl ester, known as Fesoterodine. Said document also describes the formation of their salts, particularly, the formation of Fesoterodine fumarate.

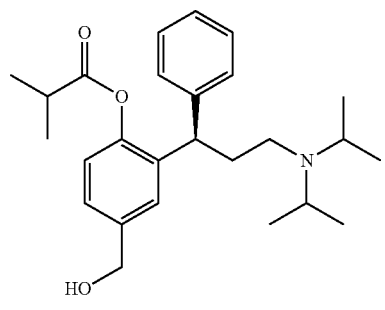

Fesoterodine

The synthetic processes described in document WO 94/11337 for the synthesis of Fesoterodine include the one depicted in Reaction Scheme 1. Said process comprises the formation of a dihydrocoumarin intermediate by coupling in acid medium, a transformation which takes place with a low yield; subsequently the introduction of the hydroxymethyl group takes place by means of reaction of a bromo-derivative with an organomagnesium compound, followed by reduction to hydroxyl:

Reaction Scheme 1

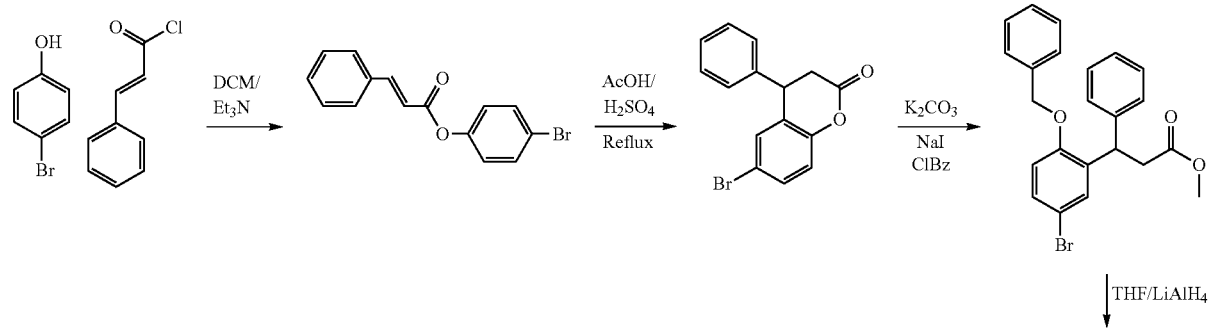

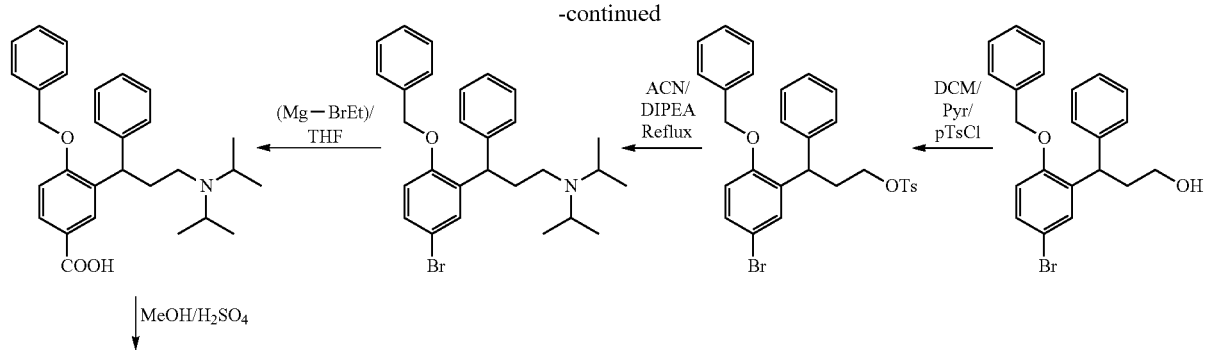

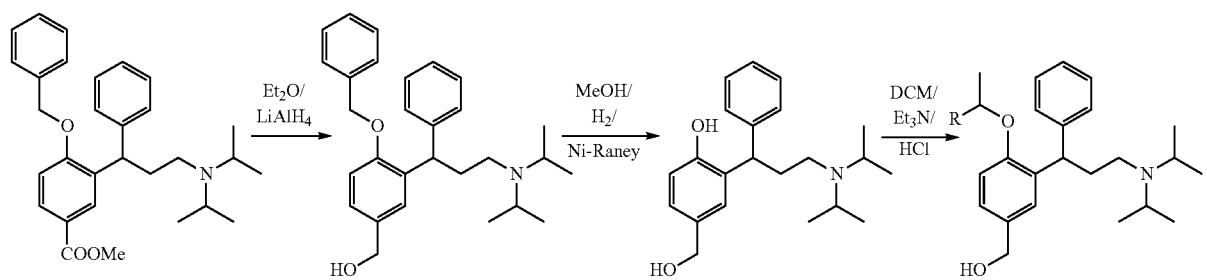

The previous process has a number of drawbacks, since it is a long and expensive synthesis, which furthermore uses reagents which are difficult to handle such as organomagnesium compounds and Ni-Raney.

An alternative process for obtaining Fesoterodine is described in patent application WO 99/58478, as is shown in Reaction Schemes 2 and 3. Said process comprises the formation of a chiral amide, on which a phenylmagnesium compound is added to give rise, after the hydrolysis of the amide group, to a chiral derivative of diphenylpropanoic acid, which by means of the formation of a tertiary amide and subsequent reduction gives rise to the 3,3-diphenylpropylamino derivative intermediate (Reaction Scheme 2).

Reaction Scheme 2

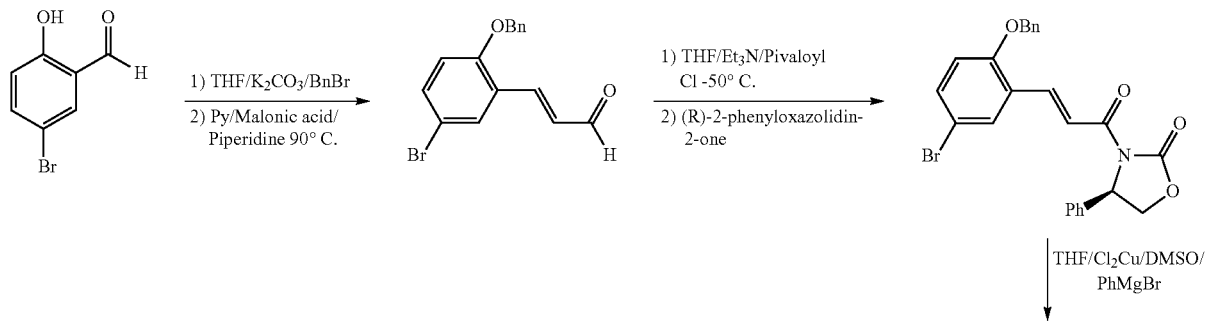

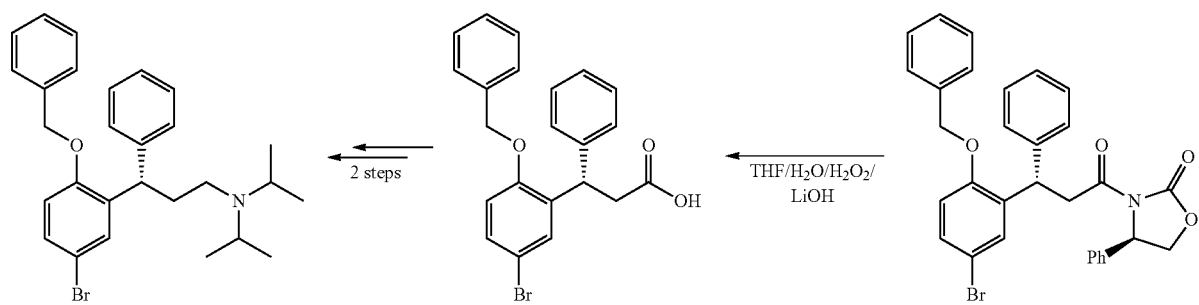

The conversion of the bromo-derivative into the hydroxymethyl group is performed through a process of metalation, carbonation and subsequent reduction of the carboxyl group obtained. Finally, the deprotection of the phenol by hydrogenation of the benzyl group and its subsequent esterification give rise to Fesoterodine (Reaction Scheme 3).

This same patent application WO 99/58478 also describes a synthesis which has fewer reaction steps to reach Fesoterodine. The process comprises a Heck reaction and the addition of phenyl-Li in a Michael type addition. However, the 2-bromoanisole derivative is a not very accessible raw material, the use of Pd reagents which make its industrialization difficult being furthermore necessary. Additionally, the global process has low or moderate yields (Reaction Scheme 4).

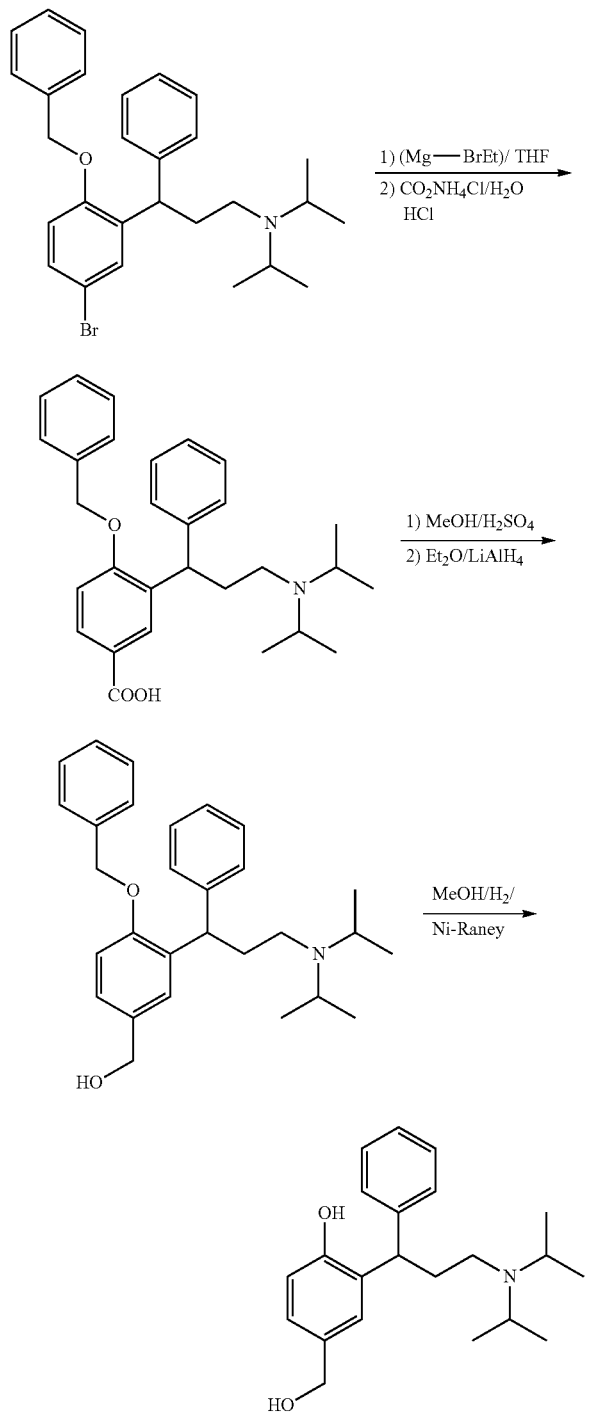

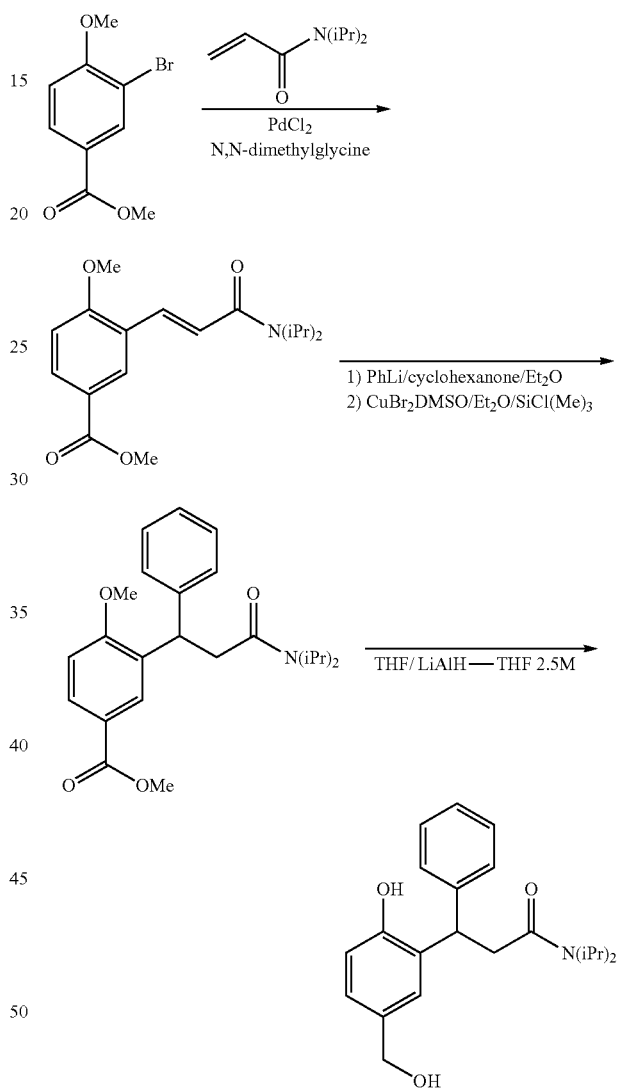

This synthesis again uses a large number of synthetic steps and uses chiral reagents, which usually have high costs, such that the industrial application of the process is difficult.

A different approach is described in European patent EP 1289929 B1, by means of a synthetic route in which a coupling in acid medium is initially performed, forming a dihydrocoumarin as a racemic intermediate. Said intermediate is then subjected to a stereoselective resolution process to obtain the suitable enantiomer. The latter is subsequently reduced to a lactol derivative, in which a diisoalkylamine is introduced by means of a reductive amination. Although the process is shorter, many synthesis steps are still required. In addition, the use of the aluminum tert-butoxide as a reducing agent is a considerable problem of toxicity and added cost to the process (Reaction Scheme 5).

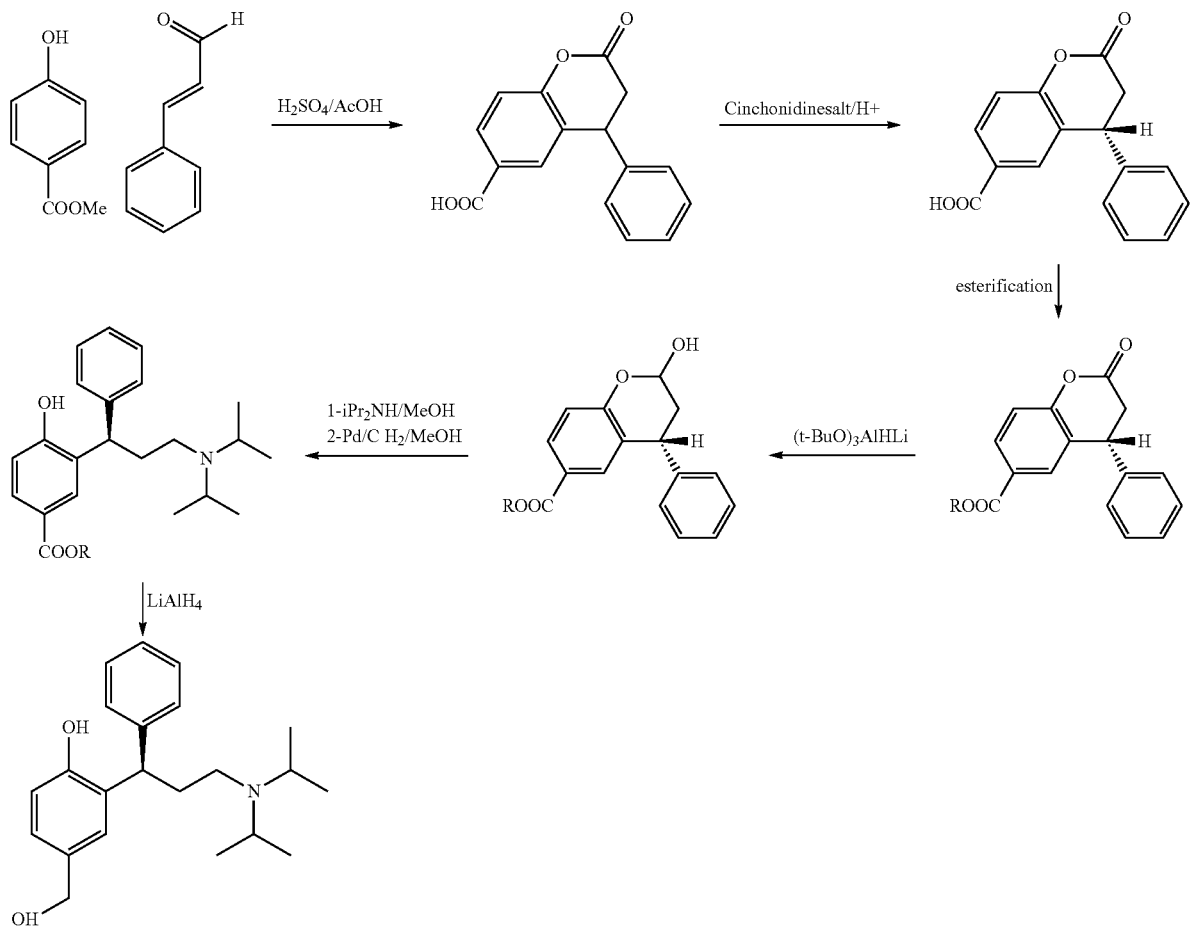
WO 2007/138440 describes a route of synthesis through the formation of a dihydrocoumarin intermediate, by means of a reaction needing conditions of reflux in toluene and toluene/hydrochloric acid for long time periods and with a low yield (Reaction Scheme 6).
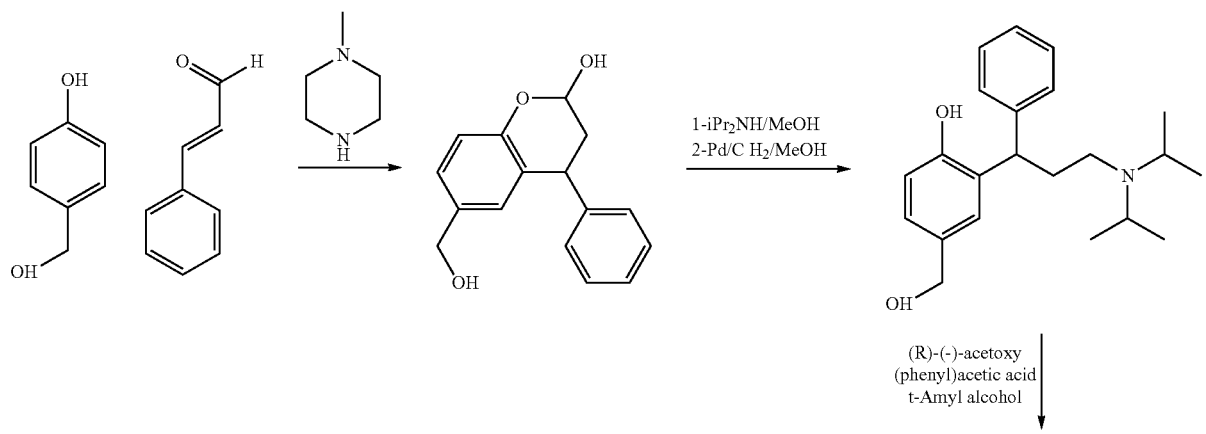

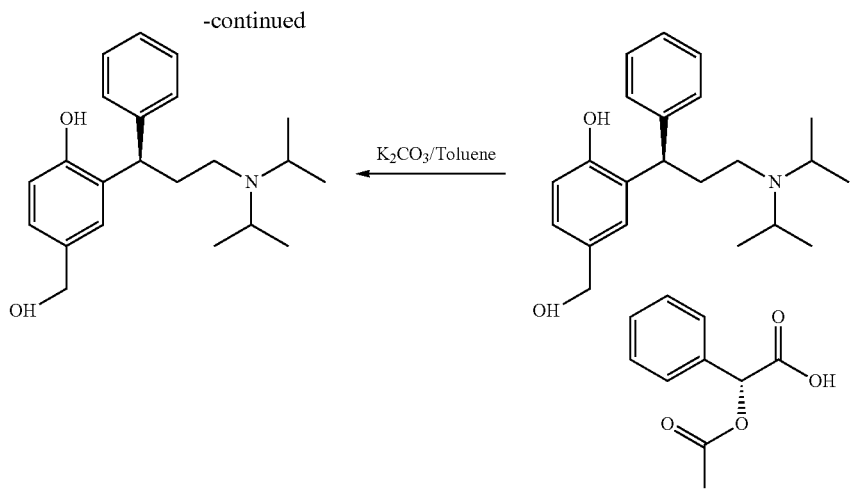

It is therefore necessary to solve the problems associated with the processes belonging to the state of the art and provide an alternative process for obtaining Fesoterodine and 3,3-diphenylpropylamine analogs which improves the synthesis of the process using more cost-effective reagents and starting materials, which furthermore allow reducing the number of steps of the synthetic route which leads to obtaining them. Advantageously, said process must be applicable at industrial scale and must provide the desired product with good yield and quality.

SUMMARY OF THE INVENTION

The invention faces the problem of providing an alternative process for obtaining 3,3-diphenylpropylamines, and particularly Fesoterodine, which overcomes all or part of the problems existing in the different aforementioned syntheses of the state of the art.

The solution provided by the present invention is based on the fact that the inventors have observed that it is surprisingly possible to efficiently obtain 3,3-diphenylpropylamines of general formula (I) (defined below), their enantiomers, solvates or salts, by means of the chemoselective reduction of the acid group against the ester group in compounds of general formula (V) (defined below). Furthermore, said compounds of general formula (V) can be suitably obtained by means of an esterification reaction.

Likewise, the present invention also provides a process for obtaining 3,3-diphenylpropylamines of general formula (I) (defined below), their enantiomers, solvates or salts, from commercial or easily accessible products, comprising: in the first place, a Friedel-Crafts type electrophilic aromatic substitution reaction between a compound of general formula (II) (defined below) and a compound of general formula (III) (defined below), whereby a compound of general formula (IV) (defined below) is obtained; if necessary, hydrolyzing the compound of general formula (IV) to give the acid of general formula (IV') (defined below); then, subjecting the compound obtained in the previous step to an esterification reaction of the hydroxyl group to give rise to the compound of general formula (V); and finally, subjecting the compound of general formula (V) to a chemoselective reduction to give the compound of general formula (I), among which Fesoterodine is included. The previously indicated transformations are shown in Reaction Scheme 7.

Reaction Scheme 7

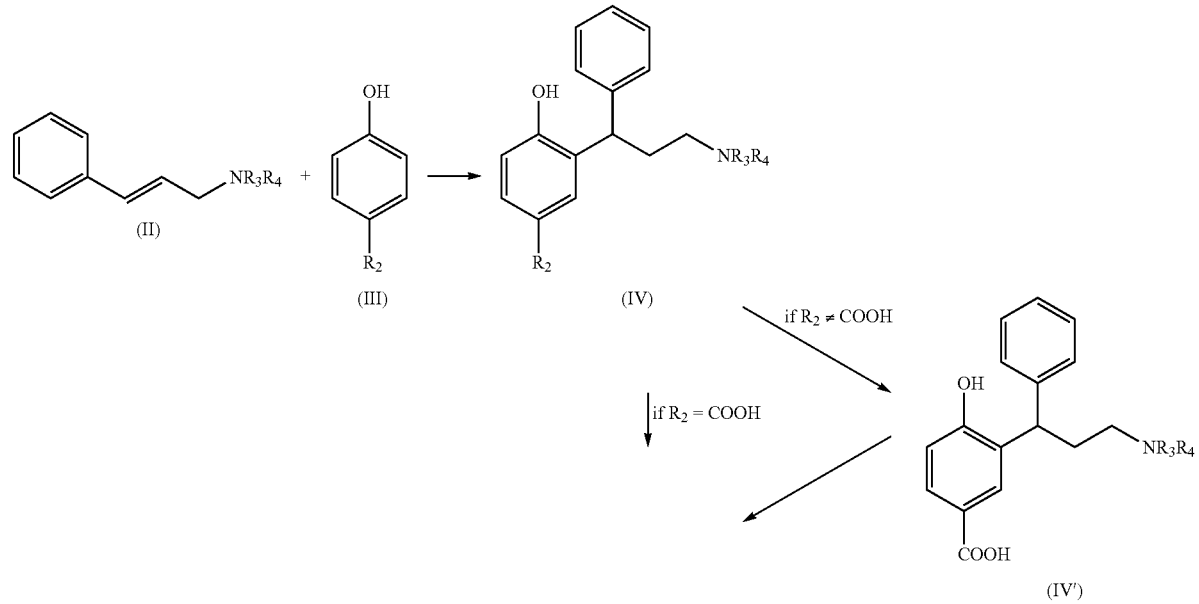

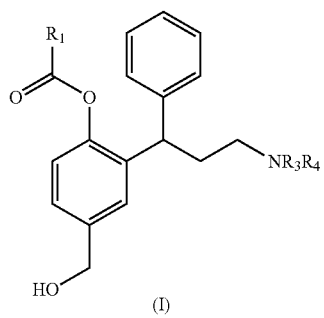 (I)

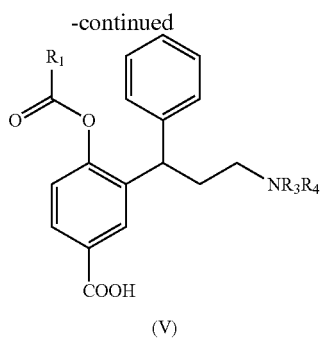 (V)

wherein
$R_1$ is $C_1$-$C_8$ alkyl;
$R_2$ is selected from CN, $COOR_5$ and $CONR_6R_7$; wherein R, is selected from H, Cl and $C_1$-$C_8$ alkyl; and
$R_6$ and $R_7$, independently of one another, are selected from H and $C_1$-$C_8$ alkyl;
$R_3$ and $R_4$, independently of one another, are selected from H and $C_1$-$C_8$ alkyl, or together form a ring of 3 to 7 members with the nitrogen to which they are bound.

As a whole, a process such as the one provided by the present invention has the advantage of considerably reducing the number of synthetic steps with respect to the processes of the state of the art, while at the same time high yields are achieved with very simple steps. Likewise, said process is not toxic and allows starting from inexpensive and non-hazardous reactants, providing 3,3-diphenylpropylamines, and, particularly, Fesoterodine, with a good yield and pharmaceutical quality. All of this contributes to reducing the overall cost of the process, making it commercially interesting and allowing it to be put into practice on an industrial level.

Therefore, in one aspect, the invention relates to a process for obtaining 3,3-diphenylpropylamines of general formula (I), their enantiomers, solvates or salts, comprising subjecting a compound of general formula (V) to a chemoselective reduction of the acid group against the ester group. In a particular preferred embodiment, said process is aimed at obtaining Fesoterodine.

In another aspect, the invention relates to a process for obtaining 3,3-diphenylpropylamines of general formula (I) (defined below), their enantiomers, solvates or salts, from said compounds of general formula (II) and (III) (defined below), as has been previously mentioned.

In another additional aspect, the invention relates to the compounds of general formula (V), their enantiomers, solvates or salts, useful in obtaining 3,3-diphenylpropylamines of general formula (I). In a preferred embodiment, the invention relates to the compounds of formula (Va) (defined below), their enantiomers, solvates or salts, particularly useful in obtaining Fesoterodine.

DETAILED DESCRIPTION OF THE INVENTION

Definitions
As used herein, the term "$C_1$-$C_8$ alkyl" relates to a radical derived from a linear or branched alkane of 1 to 8 carbon atoms, for example, methyl, ethyl, propyl, butyl, isopropyl, isobutyl, etc.

The invention also provides "salts" of the compounds described in the present description. By way of illustration, said salts can be acid addition salts, base addition salts or metal salts, and can be synthesized from the parent compounds containing a basic or acid moiety by means of conventional chemical processes known by the persons skilled in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of said acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts.

The salts can be pharmaceutically acceptable or not. The salts which are not pharmaceutically acceptable can be used as means for obtaining pharmaceutically acceptable salts.

Likewise, the compounds described in the present description can be obtained in the form of free base or acid or, alternatively, in the form of salt. In both cases they can be obtained in crystalline form, both as free compounds or as solvates (e.g., hydrates, alcoholates, etc.), both forms being included within the scope of the present invention. The solvation methods are generally known in the state of the art.

Compounds are "stereoisomers" when they are formed by the same atoms bound by the same sequence of bonds, but with different three-dimensional structures which are not interchangeable, such as for example, enantiomers or diastereoisomers.

As can be seen in the previous scheme, the compounds of general formulas (IV), (IV'), (V), (Va) and (I) comprise at least one asymmetric center and can therefore give rise to enantiomers with the spatial configuration (R) or (S). All the individual enantiomers of said compounds as well as their mixtures, e.g., their racemic mixtures, are included within the scope of the present invention. Said individual enantiomers can be separated by means of conventional techniques. Although the invention can take place using mixtures of enantiomers of said compounds of general formulas (IV), (IV'), (V), (Va) and (I), for example, their racemic mixtures, in practice it is preferred to obtain a single enantiomer of formula (I). Therefore, the process preferably comprises a separation of enantiomers from a mixture thereof; said separation can occur in any of the intermediates of the process (compounds of general formulas (IV), (IV'), (V) or (Va)) or on the end product (compounds of general formula (I)).

Likewise, depending on the substituents, the compounds of general formulas (IV), (IV'), (V), (Va) and (I) can have more than one asymmetric center and can therefore give rise to diastereoisomers. All the individual diastereoisomers of said compounds as well as their mixtures, e.g., their racemic mixtures, are included within the scope of the present invention. The individual diastereoisomers can be separated by means of conventional techniques.

The term "pharmaceutically acceptable" relates to molecular entities and compositions being physiologically tolerable and normally not causing an allergic reaction or similar adverse reaction, such as gastric discomfort, dizziness and the like, when they are administered to a human being. Preferably, as used in this description, the term "pharmaceutically acceptable" means approved by a governmental regulatory agency or listed in the US pharmacopoeia or another generally recognized pharmacopoeia for use in animals, and more particularly in humans. Pharmaceutically acceptable salts can be obtained from salts which are not pharmaceutically acceptable.

Unless otherwise indicated, the compounds of the invention also include compounds which differ in the presence of one or more isotopically enriched atoms. By way of illustration, compounds having the structures defined herein, with the exception of the substitution of at least one hydrogen with a deuterium or with tritium, or the substitution of at least one carbon with a carbon enriched in $^{13}C$ or $^{14}C$, or at least one nitrogen with a nitrogen enriched in $^{15}N$, are within the scope of this invention.

Obtaining a Compound of General Formula (IV)

The compounds of general formula (II) can be easily obtained by following Example 1 of application WO 2007/017544 or by methods described in the state of the art such as: *Chemistry Letters*, 1995, 1121-2; *Organic Chemistry and Biochemistry*, 1995, 40 (3), 190-5 and *Tetrahedron*, 2000, 56, 4893-4905.

The compounds of general formula (III) are known and are commercially available.

The reaction of the propylenephenylamine of general formula (II) with the disubstituted aromatic hydrocarbon of general formula (III) is a Friedel-Crafts type electrophilic substitution reaction of the ortho position of the aromatic ring present in the compound of formula (III), and is carried out in a reaction medium comprising an acid acting as a catalyst of said Friedel-Crafts type electrophilic aromatic substitution reaction. Virtually any type of acid can be used. This reaction generally takes place with a high yield, typically comprised between 70% and 90%, thus contributing to the high overall yield of the process for obtaining the compound of formula (I) provided by this invention when it is carried out from said compounds of general formulas (II) and (III).

In a particular embodiment, said acid is an inorganic acid. Illustrative non-limiting examples of inorganic acids which can be used include hydrobromic, perchloric, sulfuric, hydrochloric, phosphoric acids, etc., and mixtures thereof. Said inorganic acids can be used in the form of solutions or aqueous suspensions.

In another particular embodiment, said acid is an organic acid, advantageously, a strong organic acid. Illustrative non-limiting examples of organic acids which can be used include sulfonic acids, such as p-toluenesulfonic acid, methanesulfonic acid, trifluoromethanesulfonic acid, trifluoroacetic acid, etc., and mixtures thereof.

In another particular embodiment, the reaction medium comprises one or more inorganic acids and one or more organic acids. In a more particular embodiment, the reaction medium comprises an inorganic acid selected from the group consisting of hydrobromic acid, perchloric acid, sulfuric acid, hydrochloric acid, phosphoric acid and mixtures thereof, and an organic acid, such as, for example, acetic acid, trifluoroacetic acid, methanesulfonic acid, etc., and mixtures thereof.

The reaction is carried out in a suitable reaction medium. In a particular embodiment, said reaction medium comprises, in addition to the acid acting as a catalyst, a solvent, for example, acetic acid or an alcohol, such as an alcohol of 1 to 5 carbon atoms.

In a particular embodiment, the reaction medium comprises acetic acid as a solvent and sulfuric acid as a catalyst. In another particular embodiment, the reaction medium comprises an alcohol as a solvent, e.g., ethanol or isopropanol, and sulfuric acid as a catalyst.

The electrophilic aromatic substitution reaction between the compound of general formula (II) and the compound of general formula (III) is carried out in different conditions.

Thus, in a particular embodiment, the electrophilic aromatic substitution reaction between the compounds of general formulas (II) and (III) is carried out using between 1 and 6 equivalents of the compound of general formula (III) per equivalent of compound of general formula (II), in a reaction medium comprising an inorganic acid, for example, perchloric acid, sulfuric acid, hydrochloric acid, phosphoric acid or mixtures thereof, preferably sulfuric acid, at a temperature comprised between 80° C. and the reflux temperature, preferably at the reflux temperature, in the presence of a solvent, for example, an alcohol (e.g., ethanol or isopropanol), or preferably acetic acid.

In another particular embodiment, the electrophilic aromatic substitution reaction between the compounds of general formulas (II) and (III) is carried out using between 1 and 6 equivalents of the compound of general formula (III) per equivalent of compound of general formula (II), and an organic acid, for example, p-toluenesulfonic acid, methanesulfonic acid, trifluoromethanesulfonic acid, etc., preferably trifluoromethanesulfonic acid, and a solvent, such as acetic acid, at a temperature comprised between 60° C. and the reflux temperature, preferably between 60° C. and 90° C.

The compound of general formula (IV) has a chiral carbon and can therefore exist either in the form of its isolated (R) or (S) enantiomers or in the form of mixtures of said enantiomers. As used in this description, the term "mixtures of enantiomers" or "enantiomeric mixtures" includes both the racemic mixtures and the mixtures enriched in any one of the enantiomers. The (R) and (S) enantiomers of the compound of general formula (IV) obtained can be separated, if desired, by conventional resolution methods for mixtures of enantiomers, for example, by means of fractional crystallization, conventional chromatographic methods, etc. In a particular embodiment, the compound of general formula (IV) obtained by means of the process provided by this invention can be obtained in the form of a mixture of enantiomers, for example, in the form of a racemic mixture. Therefore, if desired, the mixture of enantiomers obtained can be resolved into its corresponding enantiomers to obtain the desired enantiomer. In a particular embodiment, said enantiomer is the enantiomer 2-[(1R)-3-N,N-diisopropylamine-1-phenylpropyl]-4-carboxyphenol ((R)-IV'a):

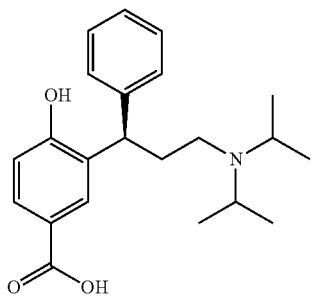

((R)-IV'a)

The resolution of the mixture of enantiomers can be performed preferably by means of the use of optically active acids, which are capable of forming a salt with the amino group present in the compounds of general formula (IV), since said formed salts are diastereomeric, they can have solubilities different from one another which allow their separation by crystallization and subsequent recovery of the desired enantiomer by filtering the precipitated diastereomeric salt and neutralization thereof in basic or acid medium, or by means of the recovery from the mother liquor (if the salt formed with the enantiomer of interest is the one remaining in solution) and subsequent neutralization.

In theory, any optically active acid capable of forming diastereomeric salts with the amine of general formula (IV) can be used. Illustrative non-limiting examples of said acids comprise the use of for example L-tartaric acid, D-10-camphorsulfonic acid, D-ditoluyltartaric acid, (R)-(−)-acetoxylphenylacetic acid, etc.

In certain conditions the reaction between the compounds of general formulas (II) and (III) takes place with the hydrolysis of the $R_2$ substituent. It is thus possible to start from a compound of formula (III) in which $R_2$ is COOR, wherein $R_5$ is Cl or $C_1$-$C_8$ alkyl, or $R_2$ is $CONR_6R_7$, wherein $R_6$ and $R_7$, independently of one another, can be H or $C_1$-$C_8$ alkyl, to give rise to a compound of general formula (IV) in which $R_2$ is a carboxylic acid group (COOH). It is also possible to start from a compound of general formula (III) in which $R_2$ is CN, to give rise to a product of general formula (IV) in which $R_2$ is a carboxylic acid group or a primary amide, depending on the reaction conditions.

Obtaining a Compound of General Formula (IV')

The compounds of general formula (IV) in which $R_2$ is a CN or $COOR_5$ group, wherein $R_5$ is Cl or $C_1$-$C_8$ alkyl, or in which $R_2$ is $CONR_6R_7$, wherein $R_6$ and $R_7$, independently of one another, can be H or $C_1$-$C_8$ alkyl, need to be initially transformed into a compound in which $R_2$ is a COOH group as a step prior to the aforementioned esterification. These compounds are susceptible of being transformed into the corresponding compounds of general formula (IV') (compounds of general formula (IV) wherein $R_2$ is COOH) in basic or acid hydrolysis conditions.

Basic hydrolysis conditions include, by way of a non-limiting illustration, the use of bases such as NaOH or KOH, in an aqueous medium or in a medium comprising a water/solvent mixture, wherein the solvent can be an alcohol, such as an alcohol, for example, an alcohol of 1 to 5 carbon atoms, e.g., methanol (MeOH), ethanol (EtOR), etc., a glycol (e.g., ethylene glycol, etc.), an ether, e.g., tetrahydrofuran (THF), etc., at a temperature comprised between room temperature (approximately 18-22° C.) and the reflux temperature of the chosen solvent.

Acid hydrolysis conditions include, by way of a non-limiting illustration, the use of acids such as hydrochloric acid, sulfuric acid, etc., in an aqueous medium or in a medium comprising a water/solvent mixture, wherein the solvent can be an alcohol, such as an alcohol, for example, an alcohol of 1 to 5 carbon atoms, e.g., methanol (MeOH), ethanol (EtOH), etc., an ether, e.g., tetrahydrofuran (THF), etc., and generally any solvent which is completely or miscible with water and which does not have groups susceptible of being hydrolyzed, at a temperature comprised between room temperature and the reflux temperature of the chosen solvent.

Obtaining a Compound of General Formula (V)

The compounds of general formula (IV) in which $R_2$ is COOH, i.e., the compounds of general formula (IV') can be subjected to an esterification reaction to give the compounds of general formula (V). The esterification can be performed either in acid medium or in basic medium by conventional methods known by the persons skilled in the art.

Said esterification reaction can be performed using carboxylic acids, esters, acid chlorides, acid anhydrides or other activated acid derivatives which react with the phenol group to give an ester. Reagents useful for the esterification reaction include, by way of a non-limiting illustration, those depicted below:

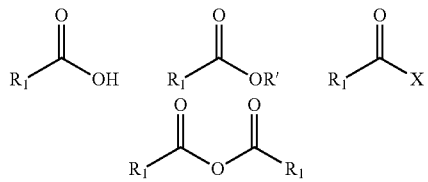

wherein $R_1$ and R', independently of one another, are $C_1$-$C_8$ alkyl; and

X is a leaving group such as Cl, Br, imidazo, thioderivative, etc.

The esterification in acid medium comprises, for example, the use of a carboxylic acid, a catalyst such as p-toluene-sulfonic acid, and a solvent which allows removing the water formed during the reaction by means of distillation, or a solvent and a dehydrating agent such as sodium sulfate, molecular sieves, etc. Said reactions generally take place at reflux temperatures of the solvent.

The esterification is preferably performed in basic medium, using organic bases as triethylamine, diisopropylethylamine, pyridine, etc., in the presence of an activated acid such as an acid chloride, an anhydride, etc., in an organic non-protic solvent such as a halogenated hydrocarbon (e.g., dichloromethane (DCM), etc.), an ether (e.g., THF, etc.), an aromatic hydrocarbon (e.g., toluene, etc.), etc.

In a preferred embodiment, the esterification reaction is performed with triethylamine and an acid chloride, in DCM at room temperature, wherein between 1 and 3 equivalents of acid chloride are used.

Another preferred form of esterification comprises the use of inorganic bases, such as NaOH, KOH, sodium carbonate, potassium carbonate, etc., in a non-protic polar solvent such as dimethyl sulfoxide (DMSO), dimethylformamide (DMF), THF, etc., and an acid chloride, also at room temperature.

During the reaction, both the ester of general formula (V) sought and another derivative which is the result of the formation of the ester with the hydroxyl group and the formation of the anhydride with the carboxyl group can be detected.

This latter ester-anhydride type intermediate in aqueous conditions integrally evolves to the ester of general formula (V).

The compound of general formula (V) has a chiral carbon and can therefore exist in the form of its isolated (R) or (S) enantiomers or in the form of mixtures of said enantiomers. The obtained (R) and (S) enantiomers of the compound of formula (V) can be separated, if desired, by conventional resolution methods for mixtures of enantiomers, for example, by means of fractional crystallization, conventional chromatographic methods, etc. In a particular embodiment, the compound of general formula (V) obtained by means of the process provided by this invention can be obtained in the form of a mixture of enantiomers, for example, in the form of a racemic mixture or, alternatively, in the form of a mixture enriched in one of said enantiomers. Therefore, if desired, the mixture of enantiomers obtained can be resolved into its corresponding enantiomers to obtain the desired enantiomer. In a particular embodiment, said enantiomer is the enantiomer 2-[(1R)-3-N,N-diisopropylamine-1-phenylpropyl]-4-carboxyphenol isobutyrate ((R)-Va):

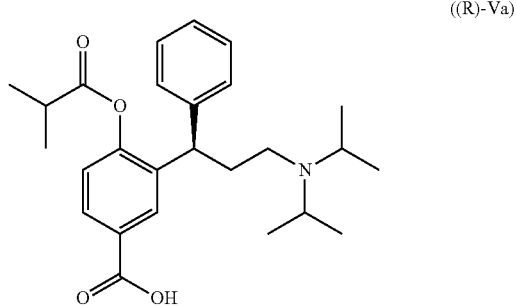 [SMILES: CC(C)C(=O)Oc1ccc(C(=O)O)cc1[C@H](CCN(C(C)C)C(C)C)c1ccccc1]

((R)-Va)

The resolution of the mixture of enantiomers can be performed by conventional methods known by the persons skilled in the art, preferably by means of the use of optically active acids which are capable of forming a salt with the amino group present in the compounds of general formula (V); since the salts thus formed are diastereomeric, they can have solubilities different from one other which allow their separation by crystallization and subsequent recovery of the desired enantiomer by filtering the precipitated diastereomeric salt and neutralization thereof in basic or acid medium, or by means of the recovery from the mother liquor (if the salt formed with the enantiomer of interest is the one remaining in solution) and subsequent neutralization.

In theory, any optically active acid capable of forming diastereomeric salts with the amine of general formula (V) can be used. Illustrative non-limiting examples of said acids comprise the use of for example L-tartaric acid, D-10-camphorsulfonic acid, D-ditoluyltartaric acid, (R)-(−)-acetoxylphenylacetic acid, etc.

Obtaining a Compound of General Formula (I)

The compound of general formula (V) can be subjected to a chemoselective reduction to give rise to the compound of general formula (I) by means of the use of a reducing agent capable of (i.e., effective for) selectively reducing the carboxyl (—COOH) group present in the compound of general formula (V).

The compound of general formula (V) contains a carboxyl (—COOH) group and an ester ($R_1$—C(O)O—) group susceptible of being reduced by means of a reducing agent. The reduction reaction on the compound of general formula (V) to give rise to the compound of general formula (I) must be chemoselective, such that the carboxyl group is preferably reduced without substantially affecting the ester group. Thus, a process for obtaining 3,3 diphenylpropylamines of general formula (I) is achieved with a smaller number of synthesis steps than those described in the state of the art.

Therefore, in the meaning used in this description, a reduction is chemoselective when the reducing agent preferably reduces the carboxyl group against the ester group; by way of illustration, the selectivity of the reducing agent towards the carboxyl group is equal to or greater than 80%, advantageously, equal to or greater than 85%, preferably, equal to or greater than 90%, more preferably, equal to or greater than 95%, even more preferably, equal to or greater than 96%, 97%, 98% or 99%.

This chemoselective reduction reaction can be carried out with different reducers, including hydrides, such as aluminum hydride ($AlH_3$), etc., or, preferably, borane (compound of boron and hydrogen), their derivatives or precursors; illustrative non-limiting examples of said borane derivatives include diborane ($B_2H_6$), borane-tetrahydrofuran ($BH_3$.THF) complexes [N. M. Yoon, C. S. Pak, H. C. Brown, S. Krishnamurthy, and T. P. Stocky, J. Org. Chem., 38, 2786 (1973)], borane-dimethyl sulfide ($BH_3$.$Me_2S$) complexes [L. M. Braun, R. A. Braun, H. R. Crissman, M. Opperman, and R. M. Adams, J. Org. Chem., 36, 2388 (1971)], etc. Likewise, illustrative non-limiting examples of borane precursors include compounds which generate borane or diborane in the reaction medium, such as, for example, $NaBH_4/I_2$, $NaBH_4/BF_3$ $(OEt)_2$, $NaBH_4/HCl$, etc., and, in short, any reducer which generates borane or diborane in the reaction medium.

The chemoselective reduction reaction is suitably carried out in a suitable solvent, such as an ether, for example, an aliphatic ether (e.g., dimethoxyethane (DME), etc.), a cyclic ether (e.g., tetrahydrofuran (THF), methyl-THF, dioxane, etc,), an aromatic solvent (e.g., toluene, etc.), or mixtures of such solvents, for example, mixtures of ethers with aromatic solvents (e.g., THF/toluene, etc.).

Said chemoselective reduction reaction can be carried out at a temperature comprised between −75° C. and 66° C., for a time period equal to or greater than 15 minutes, typically comprised between 30 minutes and 12 hours. These conditions collaborate in the reduction of the carboxyl group being selectively carried out without substantially affecting the ester group present in the compound of general formula (V).

In a preferred embodiment the chemoselective reduction reaction is performed using $NaBH_4/I_2$ in THF as a solvent, at an initial temperature of 0° C. and subsequently heating the reaction mixture to room or reflux temperature.

The compound of general formula (I) has a chiral carbon, and can therefore exist in the form of its isolated (R) or (S) enantiomers or in the form of mixtures of said enantiomers. The obtained (R) and (S) enantiomers of the compound of formula (I) can be separated, if desired, by conventional resolution methods for mixtures of enantiomers, for example, by means of fractional crystallization, conventional chromatographic methods, etc. In a particular embodiment, the compound of general formula (I) obtained by means of the process provided by this invention can be obtained in the form of a mixture of enantiomers, for example, in the form of a racemic mixture or of a mixture enriched in one of the enantiomers. Therefore, if desired, the mixture of enantiomers obtained can be resolved into its corresponding enantiomers to obtain the desired enantiomer. In a particular embodiment, said enantiomer is the enantiomer R(+)-2-(3-diisopropylamino-1-phenylpropyl)-4-hydroxymethylphenyl isobutyrate, known as Fesoterodine.

The resolution of the mixture of enantiomers can be performed by conventional methods, preferably by means of the use of optically active acids which are capable of forming a salt with the amino group present in the compounds of general formula (I); since the formed salts are diastereomeric, they can have solubilities different from one another which enable their separation by crystallization and subsequent recovery of the desired enantiomer by filtering the precipitated diastereomeric salt and neutralization thereof in basic or acid medium, or by means of the recovery from the mother liquor (if the salt formed with the enantiomer of interest is the one remaining in solution) and subsequent neutralization.

In theory, any optically active acid capable of forming diastereomeric salts with the amine of general formula (I) can be used illustrative non-limiting examples of said acids comprise the use of for example L-tartaric acid, D-10-camphorsulfonic acid, D-ditoluyltartaric acid, (R)-(−)-acetoxyphenylacetic acid, etc.

Fesoterodine fumarate is a preferred compound of formula (I) according to the process of the present invention.

According to a particular embodiment of the process of the present invention, $R_1$ is $C_1$-$C_4$ alkyl, i.e., methyl, ethyl, propyl, isopropyl, butyl, isobutyl, sec-butyl or tert-butyl; $R_1$ is preferably isopropyl.

According to another particular embodiment of the process of the present invention, $R_2$ is —COOR, wherein $R_5$ is selected from H, Cl and $C_1$-$C_8$ alkyl; $R_5$ is preferably H.

According to another particular embodiment of the process of the present invention, $R_3$ and $R_4$, independently of one another, are selected from H and $C_1$-$C_4$ alkyl, i.e., methyl, ethyl, propyl, isopropyl, butyl, isobutyl, sec-butyl or tert-butyl; $R_3$ and $R_4$ are preferably isopropyl.

According to a preferred embodiment, the invention relates to a process for obtaining Fesoterodine:

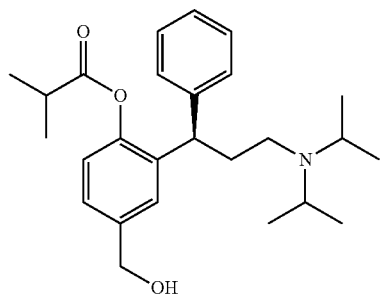 [SMILES: CC(C)C(=O)Oc1ccc(CO)cc1[C@H](CCN(C(C)C)C(C)C)c1ccccc1]

its solvates or salts, comprising:

a) reacting a compound of formula (IIa)

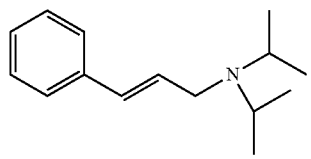

with a compound of general formula (III)

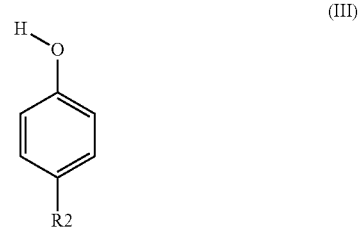

wherein $R_2$ is selected from CN, COOR$_5$ and CONR$_6$R$_7$; wherein $R_5$ is selected from H, Cl and $C_1$-$C_8$ alkyl; and $R_6$ and $R_7$, independently of one another, are selected from H and $C_1$-$C_8$ alkyl;

to give a compound of general formula (IVa)

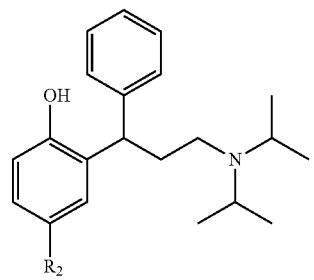

wherein R, has the previously indicated meaning;

b) if desired, separating the (R) enantiomer from the mixture of enantiomers of the compound of general formula (IVa);

c) if $R_2$ is different from COOH in the compound of general formula (IVa), subjecting said compound of general formula (IVa) to a hydrolysis to give rise to the compound of formula (IV'a)

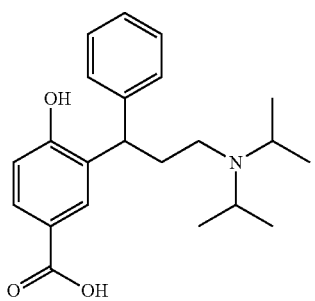

d) if desired, separating the (R) enantiomer from the mixture of enantiomers of the compound of formula (IV'a);

e) subjecting the compound obtained in the previous step to an esterification reaction of the hydroxyl group to give rise to the compound of formula (Va)

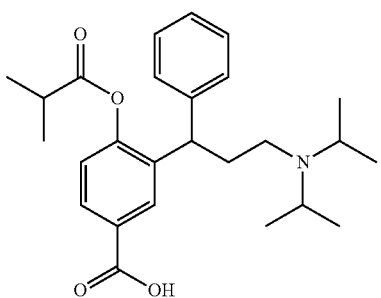
(Va)

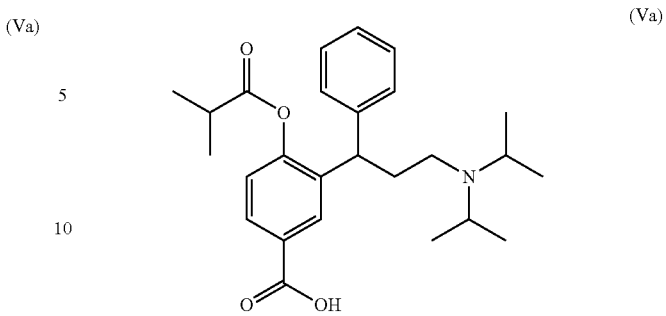
(Va)

f) if desired, separating the (R) enantiomer from the mixture of enantiomers of the compound of general formula (Va);

g) subjecting said compound of formula (Va) to a chemoselective reduction to give Fesoterodine; and h) if desired, separating the (R) enantiomer from the mixture of enantiomers of Fesoterodine and converting Fesoterodine into a salt or solvate thereof.

In another aspect, the invention relates to a compound of general formula (V)

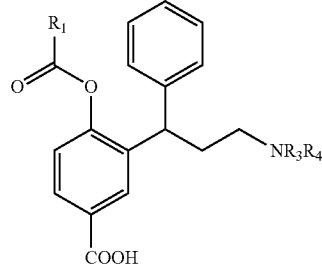
(V)

wherein $R_1$ is alkyl;

$R_3$ and $R_4$, independently of one another, are selected from H and $C_1$-$C_8$ alkyl, or together form a ring of 3 to 7 members with the nitrogen to which they are bound;

its enantiomers, solvates or salts.

The compounds of general formula (V) are useful for obtaining the compounds of general formula (I).

In a particular embodiment of the compounds of general formula (V), $R_1$ is $C_1$-$C_4$ alkyl, i.e., methyl, ethyl, propyl, isopropyl, butyl, isobutyl, sec-butyl or tert-butyl; $R_1$ is preferably isopropyl.

In another particular embodiment of the compounds of general formula (V), $R_3$ and $R_4$, independently of one another, are selected from H and $C_1$-$C_4$ alkyl, i.e., methyl, ethyl, propyl, isopropyl, butyl, isobutyl, sec-butyl or tert-butyl; $R_3$ and $R_4$ are preferably isopropyl.

The compound of formula (Va) [2-(3-N,N-diisopropylamine-1-phenylpropyl)-4-carboxyphenol isobutyrate] can be used in the preparation of Fesoterodine and is an additional aspect of this invention In a particular embodiment, the compound of formula (Va) has the spatial configuration (R) [i.e., it is the enantiomer R-(+)-2-(3-N,N-diisopropylamino-1-phenylpropyl)-4-carboxyphenol isobutyrate].

The following examples illustrate the invention and must not be considered in a limiting sense thereof.

EXAMPLE 1

Obtaining 2-(3-N,N-diisopropylamine-1-phenylpropyl)-4-carboxyphenol (IV'a)

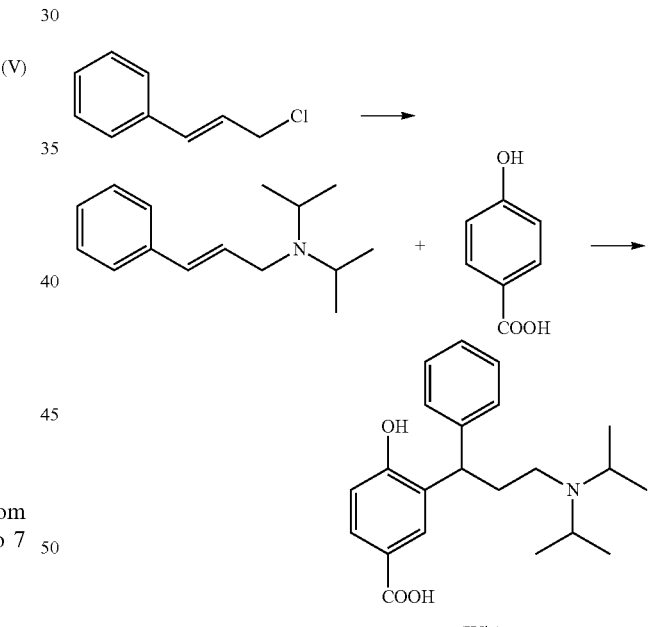

Dilsopropylamine (2.77 l, 19.65 mol) and sodium iodide (16.95 g, 0.13 mol) were loaded onto a solution of cinnamyl chloride (1 kg, 6.55 mol) in ethanol (3 l/kg) at 20/25° C. The mixture was heated at internal 80-85° C., the reaction conditions being maintained for 3-4 hours until the end of such reaction.

The mixture was cooled at 40-45° C. and distilled to an internal volume of 1.3 l. The mixture was then cooled at 20-25° C., water (4 l) and toluene (3 l) was added and the pH was adjusted to 1.0-1.5. The phases were decanted and dichloromethane (4 l) was loaded onto the aqueous phase, adjusting the pH again to 11.5-12.0. The phases were decanted and the organic phase was washed with water (4 l). Once the phases were decanted, the organic phase was distilled at atmospheric pressure to an internal volume of 1.3 l in order to then load heptane (0.5 l). Again, it was distilled to 1.3 l and heptane (2 l) was loaded.

The suspension which was obtained was filtered by a prelayer, which was washed with heptane (0.5 l). The filtered organic phase was distilled at atmospheric pressure to an internal volume of 1.3 l.

The amine content of the reaction mixture was determined by the potentiometric titration thereof.

Acetic acid (1.2 l/kg of amine), 4-hydroxybenzoic acid (0.63 kg/kg of amine, 1 equivalent), and, then, sulfuric acid (1.1 l/kg of amine, 4.5 equivalents) were loaded onto the mixture. It was heated at internal 80-85° C., the reaction conditions being maintained for 5-6 hours until the end of the reaction.

The reaction mixture was cooled to 35-40°C and water (10 l/kg of amine) and ethyl acetate (10 l/kg of amine) were loaded. The phases were decanted and the organic phase was washed out with water (5 l/kg). The aqueous phases were pooled; toluene (5 l/kg of amine) was loaded, the phases were decanted and n-butanol (10 l/kg of amine) was loaded onto the aqueous phase, the pH was adjusted to 7 and it was decanted.

The organic phase was distilled to an internal amine volume of 1.5-2.0 l/kg and then heptane (8 l/kg of amine) was loaded. The product which crystallized was cooled at 5-10° C., filtered and washed with heptane (5 l/kg of amine). The product was then dried in an oven with air circulation for 10-12 hours, obtaining a product with an overall molar yield of 40% and with a purity greater than 90%.

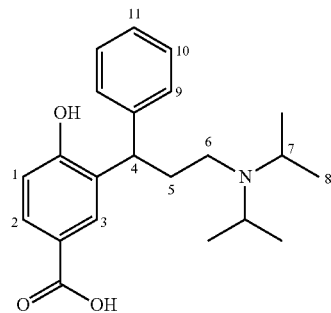 [SMILES: CC(C)N(CCC(c1ccccc1)c1cc(C(=O)O)ccc1O)C(C)C]

NMR ($^1$H) DMSO: $H_8$: doublet 0.8-0.9 ppm 12H, $H_5$: multiplet 2.0-2.1 ppm 2H, $H_6$: multiplet 2.3 ppm 2H, $H_7$: multiplet 2.8-3.0 ppm 2H, $H_4$: triplet 4.3 ppm 1H, $H_1$: doublet 6.8 ppm 1H, $H_{11}$: multiplet 7.1 ppm 1H, $H_{10-9}$: multiplet 7.1-7.3 ppm 4H, $H_2$: doublet 7.5 ppm 1H, $H_3$: singlet 7.8 ppm 1H.

NMR($^{13}$C) DMSO: 20.52; 20.57; 30.74; 36.11; 39.72; 48.04; 114.35; 125.56; 126.43; 128.59; 128.68; 129.02; 129.47; 129.77; 145.34; 157.76; 169.90.

EXAMPLE 2

Obtaining 2-(3-N,N-diisopropylamine-1-phenylpropyl)-4-carboxyphenol isobutyrate (Va)

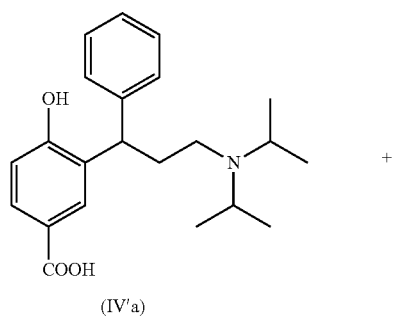

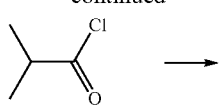

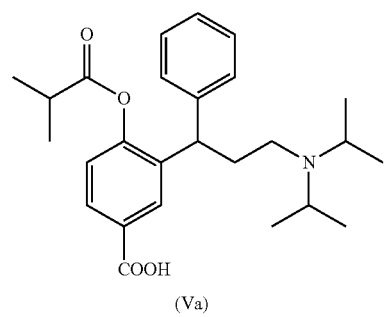

Triethylamine (0.80 l, 2.05 equivalents) was loaded onto a suspension of the amino acid obtained in Example 1 (IV'a) (1 kg) in dichloromethane (5 l). Then, without the reaction temperature exceeding 25-30° C., isobutyryl chloride (0.32 l, 1.1 equivalents) was loaded. The reaction conditions were maintained until the end of the reaction (1-2 hours). The reaction mixture was cooled and a NH$_4$Cl solution (10%) (5 l) was loaded, the pH being adjusted to 7. The product was concentrated to dryness, obtaining a residue with a purity greater than 85% and a molar yield of 95-100%.

NMR ($^1$H) DMSO: $H_{10}$: doublet 0.9-1.1 ppm 12H, $H_1$: dd 1.2-1.3 ppm 6H, $H_7$: multiplet 2.2-2.4 ppm 2H, $H_8$: multiplet 2.6 ppm 2H, $H_2$: heptuplet 2.9 ppm 1H, $H_9$: multiplet 3.2 ppm 2H, $H_6$: triplet 4.2 ppm 1H, $H_3$: doublet 7.1 ppm 1H, $H_{13}$: multiplet 7.2 ppm 1H, $H_{11-12}$: multiplet 7.2-7.3 ppm 4H, $H_4$: doublet 7.8 ppm 1H, $H_5$: singlet 8.1 ppm 1H.

NMR ($^{13}$C) DMSO: 18.65; 18.79; 19.08; 19.25; 33.47; 34.22; 40.75; 43.54; 50.14; 122.50; 126.37; 127.71; 128.27; 128.47; 128.98; 132.55; 135.90; 143.19; 150.59; 167.80; 174.60.

EXAMPLE 3

Obtaining Isobutyric Acid 2-(3-N,N-diisopropy-lamino-1-phenylprogyl)-4-(bydroxymethyl)phenyl ester (Ia)

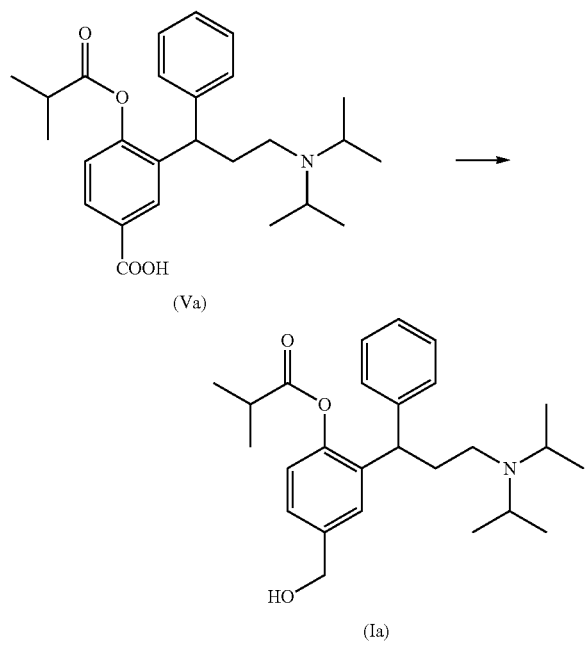

A 2 M solution of borane in THF (2.4 l, 2.0 equivalents) was slowly loaded onto a suspension at 20-25° C. of the ester obtained in Example 2 (Va) (1 kg) in THF (5 l). Once the loading had ended, the reaction temperature was increased to 60-65° C., maintaining the conditions until the end of the reaction (3-5 h). The reaction mixture was cooled and a solution of $NH_4Cl$ (10%) (5 l) was loaded, the pH being adjusted to 7. Then, ethyl acetate (5 l) was loaded and decanted. The organic phase was concentrated to dryness, obtaining a residue with a purity greater than 85% and a molar yield of 95-100%.

The invention claimed is:

1. A process for obtaining a compound of general formula (I)

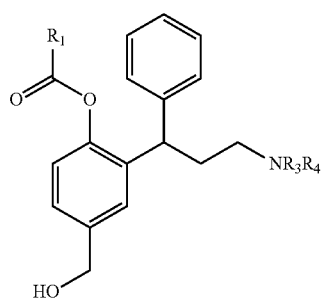

wherein
$R_1$ is $C_1$-$C_8$ alkyl; and
$R_3$ and $R_4$, independently of one another, are selected from H and $C_1$-$C_8$ alkyl, or together form a ring of 3 to 7 members with the nitrogen to which they are bound;

its enantiomers, solvates or salts, comprising subjecting a compound of general formula (V)

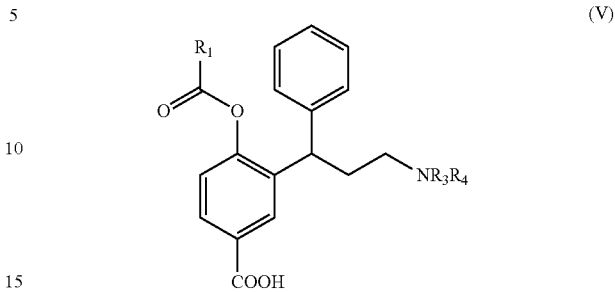

wherein
$R_1$, $R_3$ and $R_4$ have the previously indicated meaning, to a chemoselective reduction.

2. The process according to claim 1, wherein the chemoselective reduction is carried out with a reducing agent selected from a hydride, borane, a borane derivative or a borane precursor.

3. The process according to claim 2, wherein said reducing agent is selected from the group consisting of $AlH_3$, $BH_3.THF$, $BH_3.Me_2S$, $NaBH_4/I_2$, $NaBH_4/BF_3(OEt)_2$ and $NaBH_4/HCl$.

4. The process according to claim 1, additionally comprising subjecting a compound of general formula (IV')

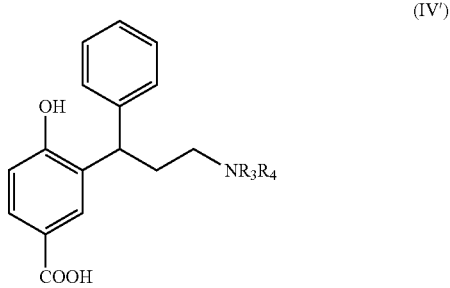

wherein
$R_3$ and $R_4$, independently of one another, are selected from H and $C_1$-$C_8$ alkyl, or together form a ring of 3 to 7 members with the nitrogen to which they are bound;
to an esterification reaction of the hydroxyl group with a carboxylic acid, an ester, an acid chloride, an anhydride or any other suitable carboxylated derivative, to obtain a compound of general formula (V)

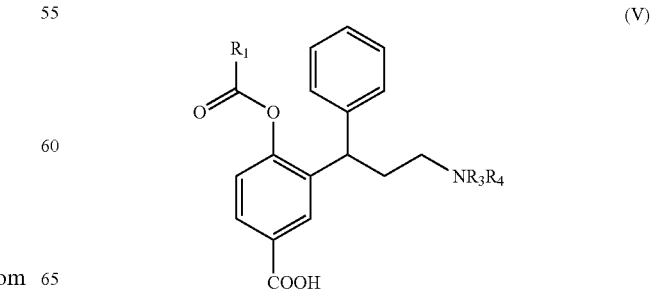

wherein

R$_3$ and R$_4$ have the previously indicated meaning.

5. The process according to claim 4, wherein the esterification reaction is carried out in a reaction medium comprising a basic medium.

6. The process according to claim 5, wherein the basic medium comprises triethylamine, diisopropylethylamine or pyridine.

7. The process according to claim 5, wherein the esterification reaction is carried out in a reaction medium comprising triethylamine, an acid chloride and dichloromethane.

8. The process according to claim 4, additionally comprising subjecting a compound of general formula (IV)

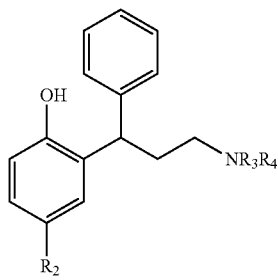
(IV)

wherein

R$_2$ is selected from CN, COOR$_5$ and CONR$_6$R$_7$; wherein
   R$_5$ is selected from H, Cl and C$_1$-C$_8$ alkyl; and
   R$_6$ and R$_7$, independently of one another, are selected from H and C$_1$-C$_8$ alkyl; and
R$_3$ and R$_4$, independently of one another, are selected from H and C$_1$-C$_8$ alkyl, or together form a ring of 3 to 7 members with the nitrogen to which they are bound;
to a hydrolysis reaction, to obtain a compound of general formula (IV')

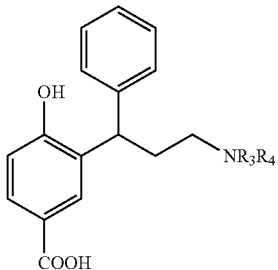
(IV')

wherein

R$_3$ and R$_4$ have the previously indicated meaning.

9. The process according to claim 8, additionally comprising reacting a compound of general formula (II)

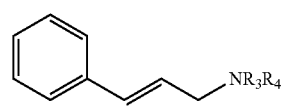
(II)

wherein

R$_3$ and R$_4$, independently of one another, are selected from H and C$_1$-C$_8$ alkyl, or together form a ring of 3 to 7 members with the nitrogen to which they are bound;

with a compound of general formula (III)

(III)

wherein

R$_2$ is selected from CN, COOR$_5$ and CONR$_6$R$_7$; wherein
   R$_5$ is selected from H, Cl and C$_1$-C$_8$ alkyl; and
   R$_6$ and R$_7$, independently of one another, are selected from H and C$_1$-C$_8$ alkyl;
to give a compound of general formula (IV)

(IV)

wherein

R$_2$ has the previously indicated meaning; and

R$_3$ and R$_4$, independently of one another, are selected from H and C$_1$-C$_8$ alkyl, or together form a ring of 3 to 7 members with the nitrogen to which they are bound.

10. The process according to claim 1, additionally comprising the separation of an enantiomer of the compound of general formula (I).

11. The process according to claim 10, wherein said enantiomer is the (R) enantiomer.

12. A process for obtaining Fesoterodine

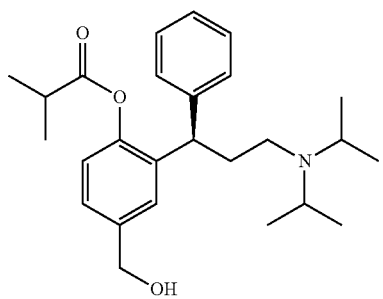 [SMILES: CC(C)C(=O)Oc1ccc(CO)cc1[C@H](CCN(C(C)C)C(C)C)c1ccccc1]

its solvates, or salts, comprising:

a) reacting a compound of formula (IIa)

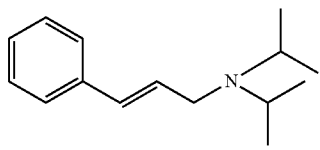
(IIa)

with a compound of general formula (III)

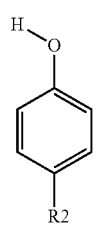
(III)

wherein
$R_2$ is selected from CN, $COOR_5$ and $CONR_6R_7$; wherein
$R_5$ is selected from H, Cl and $C_1$-$C_8$ alkyl; and
$R_6$ and $R_7$, independently of one another, are selected from H and $C_1$-$C_8$ alkyl;
to give the compound of formula (IVa)

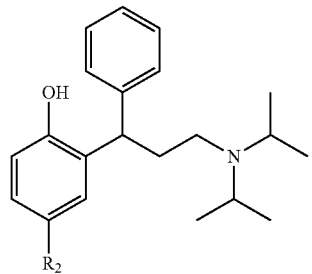
(IVa)

wherein $R_2$ has the previously indicated meaning;
b) if desired, separating the (R) enantiomer from the mixture of enantiomers of the compound of general formula (IVa);
c) if $R_2$ is different from COOH in the compound of general formula (IVa), subjecting said compound of formula (IVa) to a hydrolysis to give rise to the compound of formula (IV'a)

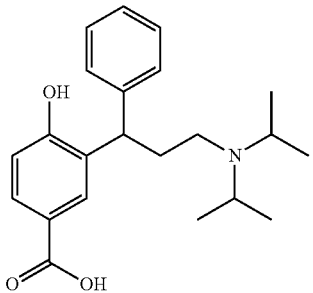
(IV'a)

d) if desired, separating the (R) enantiomer from the mixture of enantiomers of the compound of general formula (IV'a);
e) subjecting the compound obtained in the previous step to an esterification of the hydroxyl group to give rise to the compound (Va)

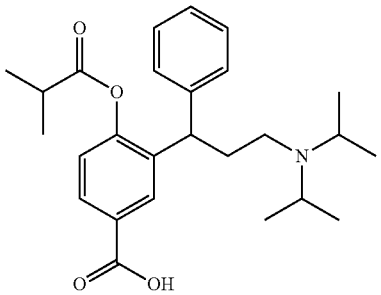
(Va)

f) if desired, separating the (R) enantiomer from the mixture of enantiomers of the compound of general formula (Va);
g) subjecting said compound of formula (Va) to a chemoselective reduction to give the compound of formula (Ia);

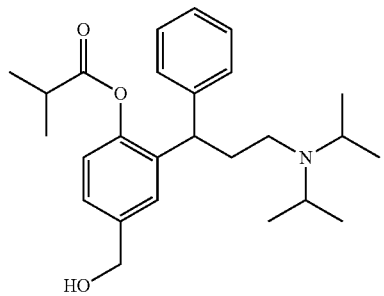
(Ia)

and
h) if desired, separating the (R) enantiomer from the mixture of enantiomers of Fesoterodine and converting Fesoterodine into a salt or solvate thereof.

13. A compound of general formula (V)

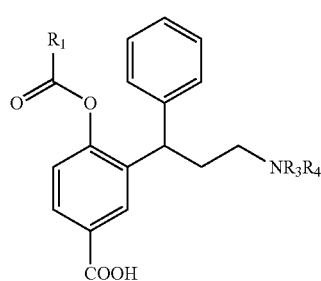
(V)

wherein
$R_1$ is $C_1$-$C_8$ alkyl;
$R_3$ and $R_4$, independently of one another, are selected from H and $C_1$-$C_8$ alkyl, or together form a ring of 3 to 7 members with the nitrogen to which they are bound;
its enantiomers, solvates or salts.

14. The compound according to claim 13 of formula (Va)

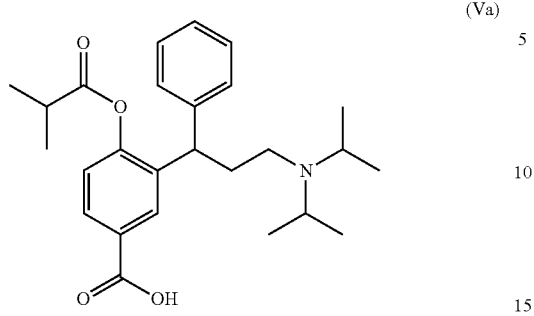

(Va)

its enantiomers, solvates or salts.

15. The process according to claim 4, additionally comprising the separation of an enantiomer of the compound of general formula (V).

16. The process according to claim 15, wherein said enantiomer is the (R) enantiomer.

17. The process according to claim 8, additionally comprising the separation of an enantiomer of the compound of general formula (IV').

18. The process according to claim 16, wherein said enantiomer is the (R) enantiomer.

19. The process according to claim 9, additionally comprising the separation of an enantiomer of the compound of general formula (IV).

20. The process according to claim 19, wherein said enantiomer is the (R) enantiomer.

* * * * *

UNITED STATES PATENT AND TRADEMARK OFFICE
CERTIFICATE OF CORRECTION

PATENT NO. : 8,722,920 B2  Page 1 of 1
APPLICATION NO. : 13/387573
DATED : May 13, 2014
INVENTOR(S) : Lorente Bonde-Larsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 275 days.

Signed and Sealed this
Twenty-ninth Day of September, 2015

Michelle K. Lee
*Director of the United States Patent and Trademark Office*